(12) United States Patent
Ortega et al.

(10) Patent No.: US 6,287,253 B1
(45) Date of Patent: Sep. 11, 2001

(54) PRESSURE ULCER CONDITION SENSING AND MONITORING

(75) Inventors: Giovani M. Ortega, Washington, DC (US); George B. Schwabe, IV; John A. Sabolich, both of Oklahoma City, OK (US)

(73) Assignee: Sabolich Research & Development, Oklahoma City, OK (US)

( * ) Notice: Subject to any disclaimer, the term of this patent is extended or adjusted under 35 U.S.C. 154(b) by 0 days.

(21) Appl. No.: 09/344,592

(22) Filed: Jun. 25, 1999

(51) Int. Cl.[7] .................................................. A61B 5/00
(52) U.S. Cl. ....................... 600/300; 128/897; 340/573.1
(58) Field of Search ............................ 600/300, 561, 600/587, 595; 128/904, 903, 897; 368/10; 340/286.07, 572.1, 275.5, 573.1

(56) References Cited

U.S. PATENT DOCUMENTS

| | | | |
|---|---|---|---|
| 3,949,388 | * 4/1976 | Fuller | 340/189 M |
| 3,974,491 | 8/1976 | Sipe | 340/272 |
| 4,080,653 | 3/1978 | Barnes, Jr. et al. | 364/417 |
| 4,175,263 | 11/1979 | Triplett et al. | 340/573 |
| 4,450,431 | * 5/1984 | Hochstein | 340/58 |
| 4,554,930 | 11/1985 | Kress | 128/774 |
| 4,610,253 | 9/1986 | Rosenberg | 128/382 |
| 4,633,237 | 12/1986 | Tucknott et al. | 340/573 |
| 4,647,918 | 3/1987 | Goforth | 340/573 |
| 4,660,568 | * 4/1987 | Cosman | 128/748 |
| 4,673,923 | 6/1987 | Boscoe et al. | 340/572 |
| 4,692,747 | 9/1987 | Wolf | 340/572 |
| 4,813,436 | 3/1989 | Au | 128/779 |
| 4,839,512 | 6/1989 | Speck | 250/231 P |
| 4,858,620 | 8/1989 | Sugarman et al. | 128/774 |
| 4,944,060 | 7/1990 | Peery et al. | 5/453 |
| 5,005,577 | * 4/1991 | Frenkel | 128/645 |
| 5,010,772 | 4/1991 | Bourland et al. | 73/862.04 |
| 5,047,750 | * 9/1991 | Hector | 340/573 |
| 5,103,210 | 4/1992 | Rode et al. | 340/572 |

(List continued on next page.)

OTHER PUBLICATIONS

M.B. Constantian et al., "Pressure Ulcers—Principles and Techniques of Management," Little, Brown and Company, Boston, Mass., pp. 7–21 (believed to be published prior to Jun. 1998).

R.N. Linder et al., "The Prevention of Pressure Sores," *Surgical Rounds*, pp. 42–48 and 55 (Jun. 1983).

J.C. Robertson et al., "An interface pressure sensor for routine clinical use," *Engineering in Medicine*, MEP Ltd., vol. 9, No. 3, pp. 151–156 (1980).

(List continued on next page.)

Primary Examiner—Eric F. Winakur
Assistant Examiner—Charles Marmor, II
(74) Attorney, Agent, or Firm—McAfee & Taft

(57) ABSTRACT

A medical sensor responds to a predetermined condition, such as pressure against a human body area susceptible to ulcer formation, and provides wireless communication of the sensing of the condition. It does this by changing a characteristic of a resonant circuit applied to the sensitive area of the human body and energized by electromagnetic induction. An electromagnetic wave transmitter of a monitoring system is disposed adjacent a support, such as a bed, for the human body. A resonant signal detector is disposed adjacent the support. The monitoring system can also comprise a controller that can compute an exposure time value and/or a shift frequency value. With the foregoing an electromagnetic field is provided across a region of the patient on the support, and resonant signals are propagated in response to the predetermined condition and the electromagnetic field and wirelessly communicated to the resonant signal detector. The information obtained from this monitoring and from a remote computer database containing a respective ulceration history for each of a plurality of patients can be used for managing the care of each patient.

57 Claims, 4 Drawing Sheets

U.S. PATENT DOCUMENTS

| | | | |
|---|---|---|---|
| 5,184,112 | 2/1993 | Guskaov | 340/573 |
| 5,224,469 | 7/1993 | Mocny | 128/55 |
| 5,253,656 | 10/1993 | Rincoe et al. | 128/782 |
| 5,323,650 | 6/1994 | Fullen et al. | 73/172 |
| 5,353,012 | 10/1994 | Barham et al. | 340/573 |
| 5,410,297 | 4/1995 | Joseph et al. | 340/573 |
| 5,510,770 | 4/1996 | Rhoads | 340/572 |
| 5,542,136 | 8/1996 | Tappel | 5/710 |
| 5,561,412 | 10/1996 | Novak et al. | 340/286.07 |
| 5,566,479 | 10/1996 | Gray et al. | 36/137 |
| 5,571,973 | 11/1996 | Taylot | 73/862.046 |
| 5,574,431 | 11/1996 | McKeown et al. | 340/572 |
| 5,608,379 | 3/1997 | Narlow et al. | 340/572 |
| 5,628,230 | 5/1997 | Flam | 73/172 |
| 5,642,096 | 6/1997 | Leyerer et al. | 340/573 |
| 5,694,952 * | 12/1997 | Lidman et al. | 128/899 |
| 5,699,038 | 12/1997 | Ulrich et al. | 340/286.07 |
| 5,745,036 | 4/1998 | Clare | 340/572 |
| 5,754,110 | 5/1998 | Appalucci et al. | 340/572 |
| 5,769,784 | 6/1998 | Barnett et al. | 600/300 |
| 5,841,350 | 11/1998 | Appalucci et al. | 340/572 |
| 6,011,477 * | 1/2000 | Teodorescu et al. | 340/573.1 |
| 6,014,346 * | 1/2000 | Malone | 368/10 |
| 6,030,351 * | 2/2000 | Schmidt et al. | 600/592 |
| 6,053,873 * | 4/2000 | Govari et al. | 600/505 |

OTHER PUBLICATIONS

Samaun et al., "An IC Piezoresistive Pressure Sensor for Biomedical Instrumentation," *IEEE Transactions on Biomedical Engineering*, vol. BME–20, No. 2, pp. 101–109 (Mar. 1973).

P. Werner et al., "Warning Mat to Signal Air Seat Cushion Failure," *Arch. Phys. Med. Rehabil.*, vol. 63, pp. 188–190 (Apr. 1982).

R. Roemer et al., "Technical note—Warning device for the prevention of ischaemic ulcers in quadriplegics," *Medical and Biological Engineering*, pp. 580–581 (Sep. 1976).

R.P. Patterson et al., "Technical note—Warning device for the prevention of ischaemic ulcers in patients who have injured the spinal cord," *Medical and Biological Engineering*, pp. 504–505 (Jul. 1973).

Publication entitled "Oxford Pressure Monitor," (3 pp.) and publication on "Skin Pressure Evaluator" (1 p.), Talley Group Limited, Lansing, Mich. (believed to be published or in public use or on sale prior to Jun. 1998).

Publication entitled "Pressure™ Monitor," Cleveland Medical Devices Inc., Cleveland, Ohio, 1 p. (believed to be published or in public use or on sale prior to Jun. 1998).

R.E. Remsburg et al., "Pressure–Relieving Strategies for Preventing and Treating Pressure Sores," *Clinics in Geriatric Medicine*, vol. 13, No. 3, pp. 513–529 (Aug. 1997).

V. Allen, et al., "Potential for Bed Sores Due to High Pressures: Influence of Body Sites, Body Position, and Mattress Design," *BJCP*, vol. 47, No. 4, 3 pp. (Jul./Aug. 1993).

D.L. Bader et al., "Effect of Externally Applied Skin Surface Forces on Tissue Vasculature," *Arch. Phys. Med. Rehabil.*, vol. 67, pp. 807–811 (Nov. 1986).

J.B. Reswick et al., "Devices and Techniques to Prevent Pressure Sores," pp. 302–311 (believed to be published or in public use or on sale prior to Jun. 1998).

* cited by examiner

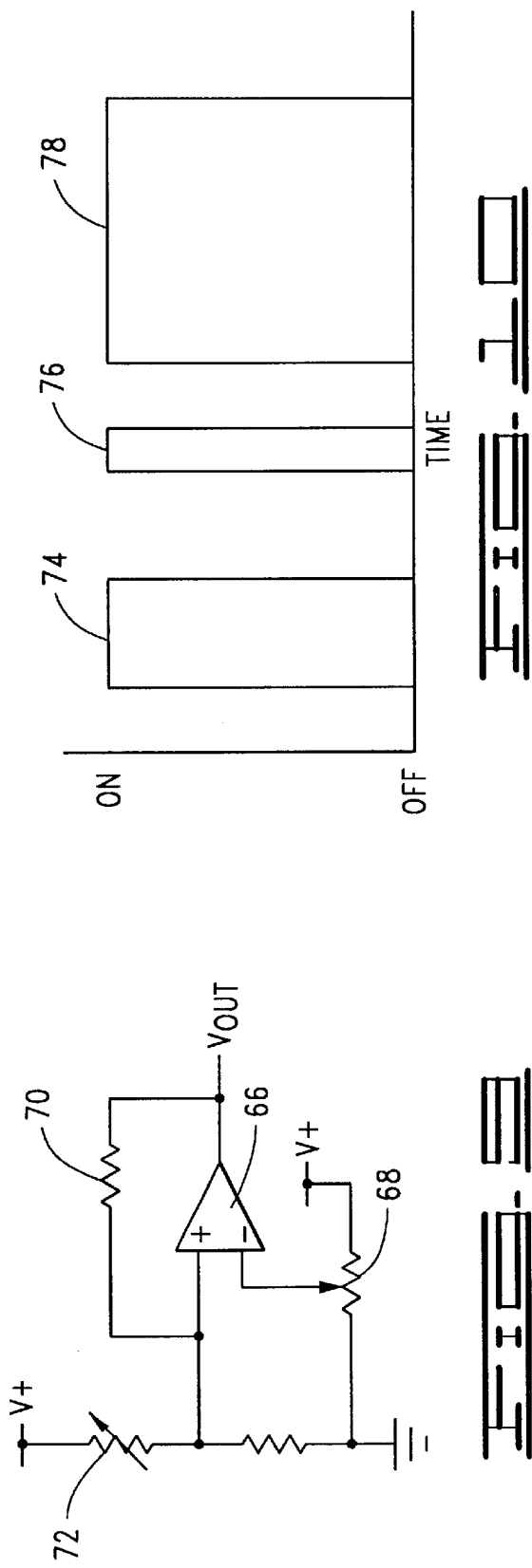

PRESSURE ULCER CONDITION SENSING AND MONITORING

BACKGROUND OF THE INVENTION

This invention relates generally to sensing and monitoring one or more conditions related to the health of the human body, such as the development, prevention and treatment of pressure ulcers. The present invention more particularly relates to a medical sensor and a system and method of monitoring one or more pressure sensitive areas of a human body. Although aspects of the present invention have application with regard to other human body conditions, the invention will be specifically described in the context of pressure that contributes to the development of external skin ulcers (e.g., decubitus ulcers). In this context, the invention also relates to a computer-implemented pressure ulcer management method.

Pressure ulcers can develop in a person who is bedridden or confined to a wheelchair, for example. Intrinsic and extrinsic factors may be involved in the development of such pressure sores. Intrinsic factors include impaired mobility, incontinence, skin condition, nutrition, and mental status.

Exposure to pressure is one extrinsic factor. When a bony, protuberant body portion, for example, is pressed against a support such as a bed or a chair under the person's weight or part of that weight, pressure is applied to that portion; if this position is maintained, such as due to the person's immobility, this pressure can be at least one contributing factor in causing a break in the person's skin, reduced blood flow to that tissue and the loss of surface tissue and the disintegration and necrosis of epithelial tissue (i.e., an ulcer).

The scope and cost of such pressure ulcers in the United States are significant. No dollar amount is placed on the cost of human suffering from this debilitating condition.

Implementation of guidelines set forth by the Agency for Health Care Policy and Research (AHCPR) has resulted in measurable improvements in carefully monitored institutions. These studies demonstrated that with diligent nursing care, many pressure ulcers are preventable. However, with staff/patient ratios typically found in nursing homes, it may be impractical to expect all aspects of the AHCPR guidelines to be followed for all but high-risk patients. Factors found to influence pressure ulcer development in one study included: inadequate numbers of nursing staff, the use of agency personnel instead of regular staff, supply shortages, and the effects of micromanagement. The extent of this problem may grow as medical advances prolong the life expectancy of seriously ill patients and as the population over the age of 65 expands. In view of the foregoing, and as an increased number of patients are given home care, there is the need for effective and simple techniques and equipment for pressure ulcer prevention.

Various equipment has been proposed or used in trying to prevent or treat pressure sores. This equipment includes overlays, replacement mattresses, and specialty beds that attempt to reduce the amount of pressure to which tissues are exposed. These may vary in effectiveness, practicality of use, and maintenance requirements. Although pertinent to the prevention and treatment of pressure sores, this particular equipment is distinct from the sensing and monitoring equipment and methods to which the present invention is directed.

Pressure sensing and monitoring systems have been proposed in, for example, U.S. Pat. No. 4,554,930 to Kress and U.S. Pat. No. 5,253,656 to Rincoe et al. Another device, a Tekscan body pressure measurement system, monitors pressure; however, the sensor construction may lend itself to limited life because creases that may be formed in it due to a peak pressure may damage the small resistive ink sensors. Furthermore, this is a relatively complex and expensive system. Less expensive pressure analyzers have been available from Talley and Cleveland Medical Devices; however, these use air bladder sensors that have a relatively high profile not recommended for continuous pressure monitoring between a patient and an adjacent support.

Accordingly, there is still the need for novel and improved equipment and methods for sensing and monitoring one or more conditions related to the health of the human body and especially related to the development, prevention and treatment of pressure ulcers. There is the particular need for a novel and improved medical sensor and system and method of monitoring one or more pressure sensitive areas of a human body. There is also the need for a computer-implemented pressure ulcer management method. These preferably should facilitate the acquisition of pressure and time information that can be used in the prevention or treatment of pressure ulcers.

SUMMARY OF THE INVENTION

The present invention meets the aforementioned needs by providing novel and improved equipment and methods for sensing and monitoring one or more conditions related to the health of the human body and especially related to the development, prevention and treatment of pressure ulcers. The present invention particularly provides a novel and improved medical sensor and system and method of monitoring one or more pressure sensitive areas of a human body. The present invention also provides a computer-implemented pressure ulcer management method. These facilitate the acquisition of pressure and time information that can be used in the prevention or treatment of pressure ulcers.

The preferred embodiment of the present invention provides real-time monitoring of pressure status over time, whereby at-risk patients requiring immediate intervention can be quickly identified. The preferred embodiment also offers the advantage of relatively inexpensive disposable sensors that safely monitor exposure time to pressure. Although disposable, the sensors are repeatedly operable during their time of use. Such sensors provide for wireless communication so that there are no wires extending from the patients to whom the sensors are attached. The sensors are thin and flexible whereby they do not add significant profile to dressings with which they are preferably used, and they do not require additional manipulation by a care provider.

Monitoring the wireless communications from the sensors permits tracking when a patient is in a position in which pressure is applied to a pressure sensitive area. Tracking can occur from different directions since a patient might move in a variety of orientations relative to the monitoring equipment. Local warnings can be given in response to defined conditions, and data can be transferred to a central location managing a network of monitored sites. Monitoring at any one site can use a plurality of sensors, and the monitoring can be on an intelligent polling basis in which no polling occurs for sensors that are not present in a particular application.

The network can be used to provide warnings to a centralized location when defined conditions are sensed and reported, to manage overall monitored information for all patients in the network, and to monitor and record patient handling schedules, for example. This can include maintaining information about specific patient ulcer history/current status, prevention or treatment protocols used, and costs related to prevention or treatment. This can also include information about how long a patient remained in a particular condition, compliance by personnel with patient schedules, and data derived from the monitored conditions.

A medical sensor of the present invention responds to a predetermined condition, and the sensor provides wireless communication of the sensing of the condition. In one embodiment, the medical sensor comprises a substrate applicable to a human body and an electric circuit connected to the substrate. The electric circuit includes: a switch operable in a circuit operative state in response to the predetermined condition; and resonant circuit elements connected to the switch as a resonant circuit to provide a signal at a resonant frequency in response to electromagnetic induction when the switch is in the circuit operative state. Such a medical sensor can be used in implementing a method of monitoring a condition of a human body. Such method comprises: changing a characteristic of a resonant circuit, applied to the human body, in response to a sensed change in the monitored condition; energizing, by electromagnetic induction, the resonant circuit such that the resonant circuit generates a resonant signal dependent on the changed characteristic; and detecting the resonant signal.

In one implementation of the aforementioned medical sensor, the switch is in a different operative state when not responding to the predetermined condition such that the resonant circuit provides a signal at another resonant frequency in response to electromagnetic induction when the switch is in the different operative state.

Although the present invention is more broadly applicable to monitoring a condition of a patent, a particular monitoring system of the present invention monitors a pressure sensitive area of a patient positioned on a support. An electromagnetic wave transmitter of the system is disposed adjacent the support. A resonant signal detector is disposed adjacent the support in operative association with the electromagnetic wave transmitter. The system also comprises a medical sensor adapted to be attached to the patient such that the medical sensor is responsive to pressure applied to the pressure sensitive area of the patient. The medical sensor includes a resonant circuit operative in at least two states in response to pressure applied to the pressure sensitive area of the patient; in at least one of the states the resonant circuit causes a resonant signal to be propagated in cooperative operation with the electromagnetic wave transmitter. The medical sensor is not tangibly attached to the electromagnetic wave transmitter or the resonant signal detector when the medical sensor is attached to the patient.

The monitoring system can also comprise a controller that is connected to the resonant signal detector such that the controller receives a respective signal from the resonant signal detector in response to the resonant signal detector detecting a respective propagated resonant signal. In one implementation, the controller computes an exposure time value in response to a predetermined exposure time monitoring period and the cumulative time within the exposure time monitoring period during which the controller receives signals from the resonant signal detector indicating pressure applied to the pressure sensitive area greater than a predetermined magnitude. In addition or alternatively, the controller can compute a shift frequency value in response to a predetermined shift frequency monitoring period and the number of transitions relative to receiving signals from the resonant signal detector during the monitoring period.

In accordance with another definition of the present invention, a method of monitoring one or more pressure sensitive areas of a patient on a support comprises: providing an electromagnetic field across a region of the patient on the support; and propagating, in operative association with the electromagnetic field, resonant signals in response to pressure above a predetermined magnitude at one or more external areas of the patient susceptible to ulceration and wirelessly communicating the resonant signals to a resonant signal detector disposed adjacent the support. In a particular embodiment, providing an electromagnetic field includes transmitting radio frequency signals having different respective frequencies within a predetermined frequency range; and propagating resonant signals includes emitting from each respective external area resonant signals having a respective resonant frequency responsive to a respective frequency of the radio frequency signals.

Another definition of the present invention includes a method of monitoring at least one pressure sensitive area of a patient on a support, comprising providing an electromagnetic field across a region of the patient on the support, and propagating, in operative association with the electromagnetic field, respective resonant signals in response to respective pressure magnitudes at the at least one pressure sensitive area of the patient and wirelessly communicating the resonant signals to a resonant signal detector disposed adjacent the support.

The present invention also provides a method of monitoring for a sensor adapted to be attached to a patient. This method comprises transmitting, across a region in which a patient is disposed, a driving signal having at least one frequency to which a sensor adapted to be attached to the patient is responsive if the sensor is attached to the patient. This method further comprises detecting whether a first response signal is emitted from the sensor in the region in response to the driving signal, the first response signal indicating the presence of the sensor in the region. This method also comprises detecting whether a second response signal is emitted from the sensor in the region in response to the driving signal, the second response signal indicating a condition related to the patient. This method can still further comprise: repeating the transmitting and detecting steps for respective selected frequencies of the driving signal and respective responsive frequencies for the first and second response signals for a plurality of sensors adapted to be attached to the patient.

The present invention still further provides a computer-implemented pressure ulcer management method. This method comprises: maintaining in a computer a database containing a respective ulceration history for each of a plurality of patients, each ulceration history including data identifying information relevant to the respective patient's susceptibility to ulcer formation; monitoring the patients, including for each patient sensing pressure application to at least one location on the respective patient at risk to ulcer formation and communicating additional data to the computer in response to sensed pressure application; storing in the computer the additional data with the data in the database; and managing the care of each patient in response to that patient's respective ulceration history and the respective stored additional data.

In one aspect of the pressure ulcer management method, each ulceration history further includes respective patient historical data identifying any unhealed ulcers, previous ulcers, when each previous ulcer was detected, when each previous ulcer was healed, the number of pressure applications sensed during the period between when a respective previous ulcer was detected and when the respective previous ulcer was healed, and the cumulative exposure time to pressure during the period between when a respective previous ulcer was detected and when the respective previous ulcer was healed. Furthermore, the additional data can include the number of pressure applications and a cumulative exposure time to pressure for each unhealed ulcer. In this context, managing the care of each patient includes computing an estimated remaining treatment period for a respective unhealed ulcer in response to the historical data for at least one previous ulcer of the patient and the additional data for the respective unhealed ulcer.

In another aspect of the pressure ulcer management method, each ulceration history further includes historical data identifying previous ulcers, the number of previous ulcers occurring at the same location of the respective patient, when each previous ulcer was detected at the respective location, and when each previous ulcer was healed. In this context, managing the care of each patient includes determining in the computer a respective frequency of ulcer formation in response to the historical data for each location; and managing the care of each patient further includes determining in the computer a respective time since the last previous ulcer was healed at each respective location for the respective patient and comparing the determined time with the respective determined frequency of ulcer formation for the respective location.

Another definition of the computer-implemented pressure ulcer management method comprises: maintaining in a computer a database containing a respective predetermined ulceration event for each of a plurality of patients; monitoring the patients, including for each patient sensing pressure application to at least one location of the respective patient susceptible to ulceration and communicating data to the computer defining shifts of the respective patient between pressure-on and pressure-off events relative to the at least one location in response to sensed pressure application; and correlating in the computer the communicated data with the respective predetermined ulceration event for each of the patients. In one aspect, the predetermined ulceration event includes a time the respective patient is to be turned relative to the respective at least one location susceptible to ulceration; and correlating the communicated data with the respective predetermined ulceration event includes determining whether a transition from a pressure-on event to a pressure-off event occurred at the respective time. In another aspect, the predetermined ulceration event includes a pressure-on threshold relative to the respective at least one location susceptible to ulceration; and correlating the communicated data with the respective predetermined ulceration event includes determining the length of time from a sensed pressure exceeding the predetermined pressure-on threshold to the next sensed pressure-off event.

Therefore, from the foregoing, it is a general object of the present invention to provide novel and improved equipment and methods for sensing and monitoring one or more conditions related to the health of the human body and especially related to the development, prevention and treatment of pressure ulcers. Another object of the present invention is to provide a novel and improved medical sensor and a novel and improved system and method of monitoring one or more pressure sensitive areas of a human body. A further object of the present invention is to provide a novel and improved computer-implemented pressure ulcer management method. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 9 is a schematic circuit diagram for one resistive type of medical sensor.

FIG. 10 is a graph illustrating a sequence of pressure-on conditions in which a pressure above a predetermined threshold is exerted for respective lengths of time against one embodiment of the medical sensor of the present invention.

FIG. 11 illustrates one embodiment for a message string communicated in an embodiment of the present invention.

DETAILED DESCRIPTION OF THE INVENTION

The present invention can be used to respond to various conditions associated with the human body. Non-limiting examples include temperature, heart rate, and blood pressure. Localized pressure application is another example and one of particular medical significance as described above; therefore, the preferred embodiments of the present invention will be described with reference to a human body pressure condition, specifically pressure created by part or all of the weight of the human body applied at one or more predetermined locations of the human body against a support surface (e.g., a bed, a wheelchair). Particular reference is made to responding to pressure above or below a predetermined pressure magnitude applied to a pressure sensitive area susceptible to ulceration; however, reference is also made to sensing and responding to pressure throughout a range of magnitudes. In a particular implementation, a predetermined pressure magnitude is selected within the range of 4.07 kilopascals to 4.7 kilopascals and more specifically it is selected at a pressure magnitude equal to an accepted average capillary closing pressure above which blood flow is reduced.

Figure 1:
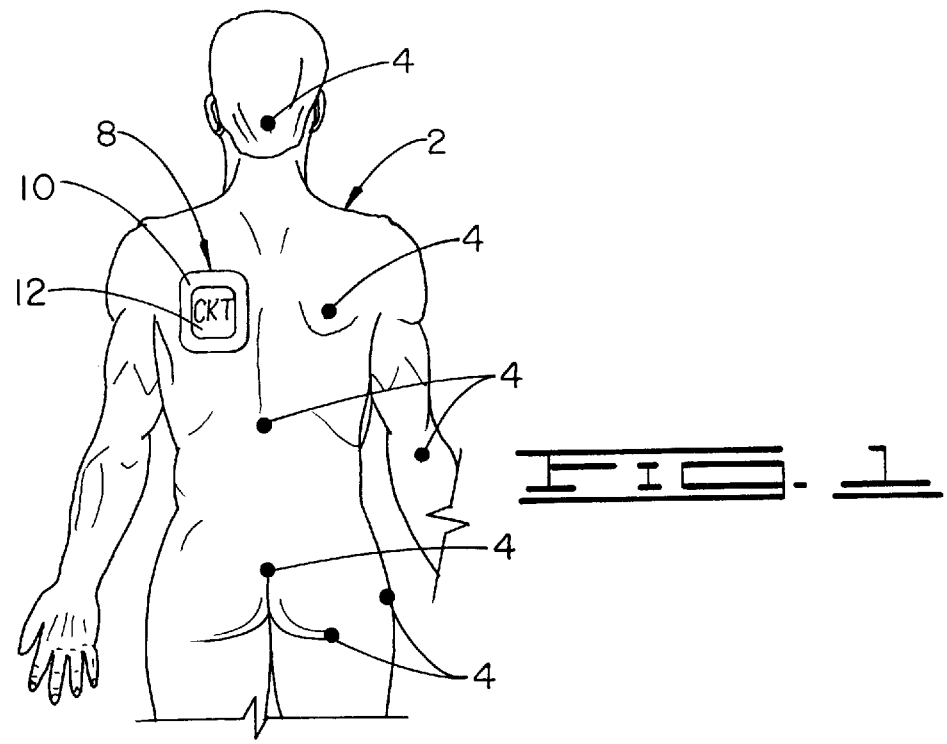
FIG. 1 illustrates part of a human body, showing some locations susceptible to pressure ulcers and showing a sensor of the present invention applied to the body at one of the locations.
Figure 2:
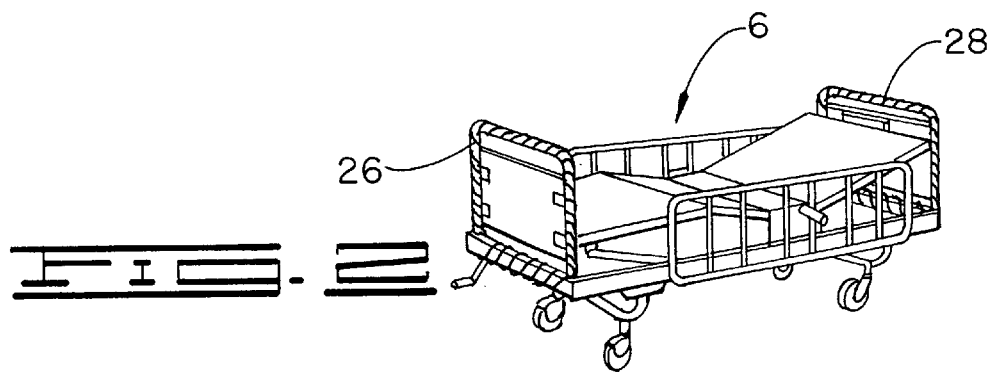
FIG. 2 illustrates one type of support, namely a bed, having part of one embodiment of the monitoring system of the present invention associated with it.
Figure 3:
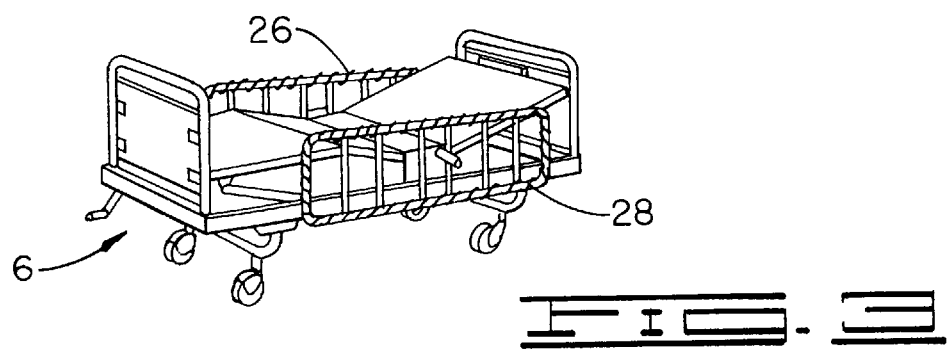
FIG. 3 illustrates the bed but having part of another embodiment of the monitoring system of the present invention associated with it.

In FIG. 1, for a person 2, circled areas 4 exemplify locations of the body susceptible to the formation of decubitus ulcers when the person is in a supine position. For the person 2, such as illustrated in FIG. 1, lying on a bed 6, such as illustrated in FIGS. 2 and 3, ulcers can occur at one or more of the pressure sensitive areas due to prolonged weight of the human body against the support surface of the bed. The body typically moves such that pressure at any one location changes repeatedly between less than a predetermined pressure magnitude and greater than the predetermined pressure magnitude. When such movement occurs frequently enough, ulcers do not tend to form; however, when the number of movements on and off a sensitive area decreases, whereby there is prolonged continuous pressure application to a respective pressure sensitive area, ulcers can form.

One aspect of the present invention includes a medical sensor that can be applied to a pressure sensitive area either before or after the formation of an ulcer. One such medical sensor is illustrated in FIG. 1 and identified by the reference numeral 8. The medical sensor 8 is shown applied to the patient's skin adjacent the posterior prominence of the left scapula of the person 2. In the illustrated embodiment, the medical sensor 8 includes a dressing 10 and a pressure responsive circuit 12 connected to the dressing 10.

The dressing 10 defines one form of a substrate applicable to the body 2. It can be of a conventional design. One non-limiting example of a specific dressing is the Restorer Plus wound care dressing (Model No. 9953 having a 4"×4" adhesive bandage) from Hollister, Inc. of Libertyville, Illinois. This type of dressing is suitable for treating stage I or stage II pressure ulcers as those stages of ulcers are defined from Agency for Health Care Policy and Research Publication No. 92-0052, 1992 (AHCPR 15: Bergstrom N., Allman R. M., Carlson C. E., et al., Pressure Ulcers in Adults: Prediction and Prevention. Clinical Practice Guideline. Quick Reference for Clinicians, No. 3. Rockville, Maryland: U.S. Dept. of Health and Human Services, Public Health Service). The present invention is not limited to use with stage I or stage II pressure ulcers, however.

In one embodiment, the pressure responsive circuit 12 can be integrally formed with the substrate, such as the dressing 10 illustrated in FIG. 1. This can be by conventional manufacturing processes adapted to bind the circuit 12 in the dressing 10. For example, if the dressing includes a molded substrate, the circuit 12 can be adapted to be placed in the mold prior to the molding of the substrate of the dressing so that the circuit ends up within the molded substrate.

In another embodiment, the pressure responsive circuit 12 can be connected by an adhesive member of the circuit 12. This can define another form of substrate applicable to the body 2. For example, the adhesive member can be attached to the outer surface of the dressing 10 as illustrated in FIG. 1, or in another embodiment the adhesive member can be attached directly to the skin of the body 2 if no dressing were needed.

Thus, the dressing 10 and the adhesive member define both alternative and cooperative forms of means for attaching to the human body such that the pressure responsive circuit is exposed to one or more occurrences of the predetermined condition, namely pressure in the preferred embodiment (and particularly pressure exceeding a predetermined pressure magnitude at the predetermined location to which the medical sensor 8 is applied).

The adhesive member has an electric circuit mounted on it. These elements are described in more detail below after the following explanation of the monitoring system of the present invention.

Figure 4:
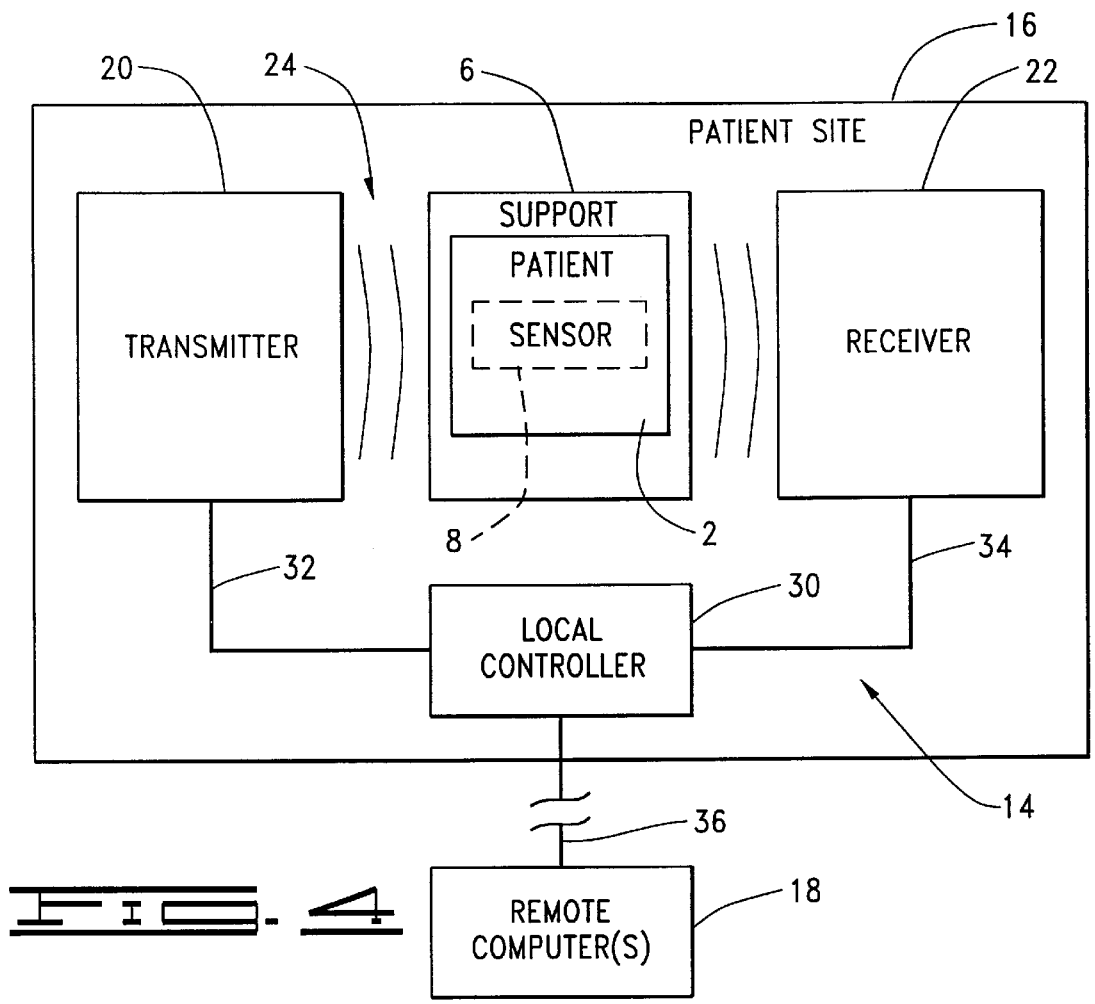
FIG. 4 is a block diagram illustrating a third association with a support for the patient as well as also illustrating an overall monitoring system.
Figure 5:
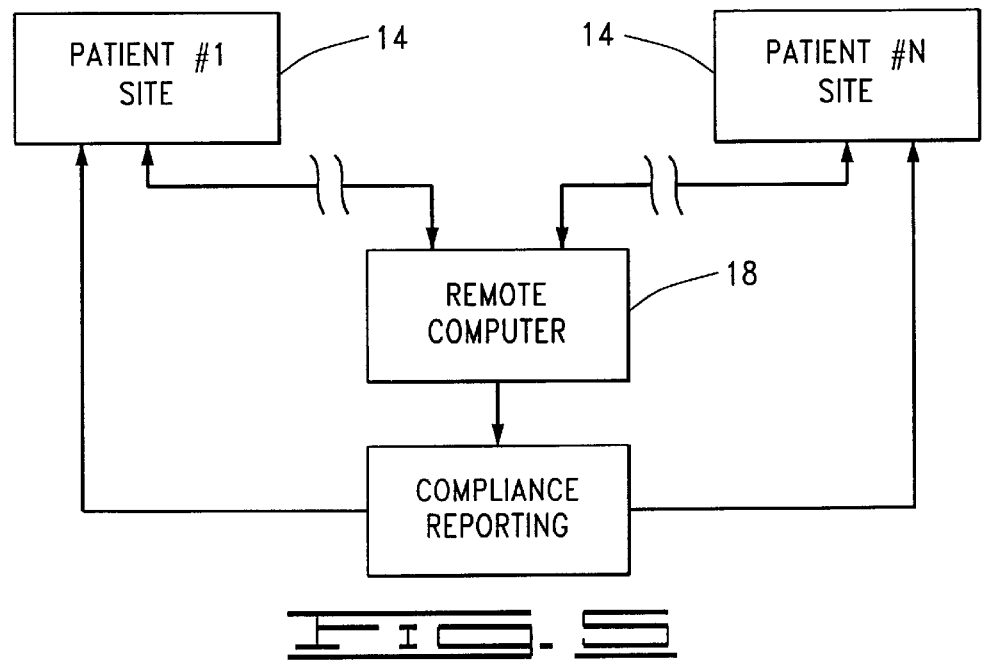
FIG. 5 is a block diagram of the monitoring system for a plurality of patients.

A monitoring system 14 at a patient site 16 is represented in FIG. 4. The system monitors one or more pressure sensitive areas of a patient, such as the person 2, positioned on a support, such as the bed 6. The representation of FIG. 4 illustrates the patient in a supine position on the support/bed 6 such that the sensor 8 is between the patient and the support and thus has pressure applied to it in response to an applicable portion of the weight of the patient on the support. Only the one monitoring system 14 will be described; however, it can connect to one or more remote computers 18 such as may be used in a computer-implemented pressure ulcer management system illustrated in FIG. 5. The remote computer 18 shown in FIG. 5 communicates with a plurality of patient sites 14. The remote computer 18 provides for system-wide compliance reporting as is described further below. The computer 18 can be of any suitable type. One non-limiting example is a conventional personal computer having a conventional operating system in which an application program for performing the applicable operations described in this specification operates; such an application program can be provided by one skilled in the art given the description herein and a specific computer and operating system. Communications to and from the computer 18 can be by any suitable technique, a non-limiting example of which is a local area network.

Referring to FIG. 4, the monitoring system 14 includes an electromagnetic wave transmitter 20 disposed adjacent the support where the patient is (e.g., to one side of the bed 6). The transmitter 20 preferably has the capability of providing a variable frequency signal. The transmitter 20 can be of any type suitable for achieving at least the transmitting operations described herein; one example is a transmitter of the type used in electronic article surveillance systems.

The monitoring system 14 also includes a resonant signal detector/receiver 22 disposed adjacent the support in operative association with the transmitter 20. For example, the receiver 22 is disposed to another side of the bed 6 in operative association with the electromagnetic wave transmitter 20 such that an electromagnetic field 24 generated by the transmitter 20 exists between the transmitter 20 and the detector 22. The receiver 22 can be of any type suitable for achieving at least the receiving operations described herein; one example is a receiver of the type used in electronic article surveillance systems.

For generating the electromagnetic field 24, the transmitter 20 uses an antenna; and for receiving signals the receiver 22 uses an antenna. Two implementations are exemplified in FIGS. 2 and 3. In FIG. 2, a coil 26 and a coil 28 are located in association with the foot and the head of the bed 6. In FIG. 3, the coils 26, 28 are associated with the side railings of the bed 6. Examples of particular implementations include wire coils wrapped externally on the bed railings as illustrated in FIGS. 2 and 3, or antenna structures mounted inside tubing of which the bed railings are made. In either embodiment of FIGS. 2 and 3, the coils 26, 28 are preferably parallel to each other and at a fixed distance to establish a sensing field, namely the electromagnetic field 24 represented in FIG. 4. In use, the sensor 8 attached to the patient 2 must be within the field between the coils 26, 28. A third implementation is illustrated in FIG. 4 in that the transmitter 20 and the receiver 22, including their respective antennas, are in stand alone units that are not mechanically connected to or part of the support 6.

It is further noted that the transmitter 20 can have a receiver capability and the receiver 22 can have a transmitter capability such that the electromagnetic field 24 can be generated from either direction (or from other directions if more than two units 22, 24 are used or if the transmitter and receiver units can be moved relative to the patient). This is useful to provide differently directed fields and sensing capabilities should the sensor 8 be closer to one side than the other such that the ability to detect a signal provided by the sensor 8 might not be detectable from the farther one of the units 20, 22.

In the implementation of FIG. 4, and as further explained below, the medical sensor 8 includes a resonant circuit operative in at least two states in response to pressure applied to the pressure sensitive area of the patient to which the medical sensor is attached. In at least one of the states, the resonant circuit propagates a resonant signal in cooperative operation with the electromagnetic wave transmitter 20. This cooperative operation is by electromagnetic induction as the medical sensor 8 is not tangibly attached to the transmitter 20 or the resonant signal detector 22 when the medical sensor 8 is attached to the patient 2.

Although only one sensor is illustrated in FIG. 4, a plurality of such sensors can be used. Each sensor is attached to the patient at a respective pressure sensitive area, such as one or more of those illustrated in FIG. 1. Each of the sensors includes a respective resonant circuit operative in the manner just described. Each, however, has its own respective resonant circuit causing its own respective resonant signal to be propagated in response to the electromagnetic field 24. Thus, if multiple sensors 8 are attached to a single patient 2, distinctive signals are provided from each sensor so that the receiver 22 and a local controller 30 are able to distinguish the signals and associate them with the respective locations on the patient 2. To enable a user to ensure that distinctive sensors are used for any one patient, each sensor of a respective resonance can be color-coded, or otherwise visually distinguished, from sensors of other resonant characteristics. A user then knows not to use the same color-coded (or other identified) sensor on any one patient.

The monitoring system 14 also includes the local controller 30, which is connected to both the transmitter 20 and the receiver 22 to control or communicate with the respective operations of these two units. The controller 30 also controls the alternating or sequential changing of the transmitter 20 and the receiver 22 to their receiving and transmitting function if the units 20, 22 are equipped as both transmitters and receivers. The controller 30 can be implemented in any suitable manner. A non-limiting example is a PIC controller programmed to provide the monitoring and signal communicating and processing tasks described for the controller 30 in this specification. Another non-limiting example is a small personal computer. Programming for these can be provided based on the descriptions in this specification. The controller 30 can also be programmed to output one or more alarms (e.g., audible, visible, tactile) if a predetermined alarm condition occurs (e.g., too long on a sensor).

The controller 30 receives respective signals from the resonant signal detector 22 (that is, whichever unit is functioning in that mode) in response to the resonant signal detector 22 detecting a respective propagated resonant signal coming from the sensor 8. The controller 30 is constructed or programmed to compute an exposure time value in response to a predetermined exposure time monitoring period and the cumulative pressure-on time within the monitoring period as determined by the controller in response to signals from the resonant signal detector representing detected propagated resonant signals indicating pressure applied to the pressure sensitive area greater than a predetermined magnitude. The controller 30 is further constructed or programmed to compute a shift frequency value in response to a predetermined shift frequency monitoring period (which may be, but need not be, the same as the exposure time monitoring period) and the number of pressure threshold transitions determined in response to signals received from the resonant signal detector during the respective monitoring period. The foregoing occurs for each medical sensor 8 when multiple ones are used with a single patient.

Whereas each sensor 8 provides wireless communication relative to the receiver 22, communications among the transmitter 20, the receiver 22 and the local controller 30 are, in the illustrated embodiment, by wire line connection. These are typically cables 32, 34 directly connected from the transmitter 20 to the controller 30 and from the receiver 22 to the controller 30; however, it is contemplated that other signal communication means, including wireless communication, can be used to interconnect these devices as well. Wireless communication can also be used between the local controller 30 and the remote computer 18; however, in the illustrated embodiment, a wired connection is shown. For example, phone line 36 can be used.

Figures 6, 7:
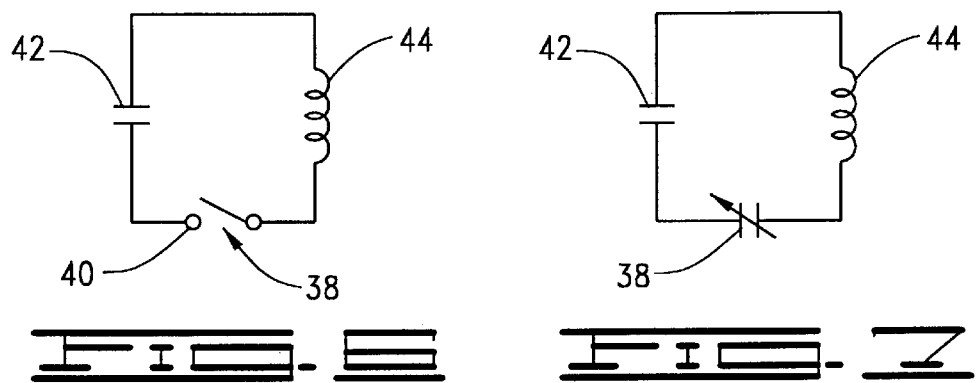
FIG. 6 is a schematic circuit diagram of one embodiment of a medical sensor of the present invention.
FIG. 7 is a schematic circuit diagram of another embodiment of a medical sensor of the present invention.

Referring next to FIGS. 6–8, preferred embodiments of the medical sensor 8 of the present invention will be described. In its implementation for responding to pressure, the medical sensor 8 is preferably mechanically operated in response to the pressure and is capable of repeated cycling among various states. The sensor is also constructed for safety in its use attached to a human being; for example, electrically active portions of the sensor are insulated against moisture, such as likely to be encountered with patients who are incontinent.

In FIG. 6, the medical sensor 8 includes a switch 38 that is operable in a circuit operative state in response to the predetermined condition. Such a switch is preferably repeatably operable between a first state and a second state in response to whether pressure above a predetermined threshold is applied by weight of the human body 2 against the support 6 such as illustrated in FIG. 4.

In FIG. 6, the switch 38 is illustrated as a device that operates in either an open-circuit state (as illustrated) or a closed-circuit state (with the illustrated switch element contacting the terminal 40). Another type of switch 38 is illustrated in FIG. 7 and identified by the same reference numeral 38 since it does function as a switch. The switch 38 of the FIG. 7 embodiment is in essence a variable capacitor having a capacitance variable between a maximum value and a minimum value (which includes zero, i.e., a short-circuit state). For the embodiment of FIG. 7, the switch 38 enables the overall circuit to always be in an operative condition as explained further below. The magnitude of the capacitance depends on the magnitude of the applied pressure. Thus, in the embodiment of FIG. 7, multiple pressure levels can be detected as different capacitance values for the switch 38 cause different operating characteristics for the overall resonant circuit.

In each of the FIG. 6 and FIG. 7 embodiments, resonant circuit elements are connected to the respective switch 38 to define a resonant circuit providing a signal at a resonant frequency in response to electromagnetic induction when the switch is in the one or more circuit operative states. This can result in multiple signals at different resonant frequencies in the case of the FIG. 7 embodiment since multiple capacitances cause different resonant signals to be generated in response to appropriate energizing frequencies in the electromagnetic field 24. The resonant circuit elements illustrated in the figures include a capacitor 42 and an inductor 44 connected with the respective switch 38 such that the circuit generates at least one respective resonant signal (i.e., an electromagnetic signal having a respective resonant frequency). The circuits defined in the FIG. 6 and FIG. 7 embodiments are self-contained so that no external wires need be connected for the circuits to operate.

In the FIG. 7 embodiment, the capacitor 42 and the switch 38 act as two capacitors in series connected across the inductor 44. Once introduced into the sensing field defined by the electromagnetic field 24, a current is induced in the circuit of FIG. 7 (and the circuit of FIG. 6 when the switch 38 is in the closed-circuit state) that resonates at its designed frequency defined by the capacitance and inductance values of the circuit elements. As pressure is applied to the switch 38 of the FIG. 7 embodiment, the overall capacitance decreases, whereby the resonant frequency increases. The different frequency signals can be detected to indicate different operative states of the switch and thus different pressures. Such change occurs until the predetermined pressure that places the switch 38 in its minimum capacitance state is reached. This state is maintained until the pressure decreases below the threshold at which the switch 38 is placed in its minimum capacitance state. Thus, the circuit of FIG. 7 can be used to provide actual pressure information as indicated by different resonant signals being detected, or it can be used in a discrete two-state manner in which a predetermined pressure magnitude places the switch 38 in its minimum capacitive state such that pressure below that magnitude defines a "pressure-off" condition for the patient 2 and a pressure above the predetermined magnitude defines a "pressure-on" condition for the patient 2.

It is in this two-state operation that the FIG. 6 circuit works. Until the predetermined pressure necessary to close the switch 38 is reached, the circuit of FIG. 6 does not generate any signal (or, it is possible that an open switch can provide capacitance whereby a signal is generated, but not one of the same frequency as the pressure-on signal, and still two-state operation is provided), thereby indicating a "pressure-off" state for the patient 2. When the predetermined pressure magnitude is applied to the switch 38 of the FIG. 6 circuit, the switch 38 moves to its closed-circuit state, whereupon a respective resonant signal is emitted from the circuit, thereby indicating the pressure-on condition for the patient 2.

More than one switch can be used in a circuit. If more are used, they are preferably connected in parallel so that if any one responds to pressure, the respective resonant signal results. This is useful if one sensor is to be applied to a relatively large area such that damaging pressure could be applied at different points across the area. Of course, the effects of various capacitances being possible in the FIG. 7 embodiment need to be addressed in such a multiple switch configuration.

Figures 8A, 8B:
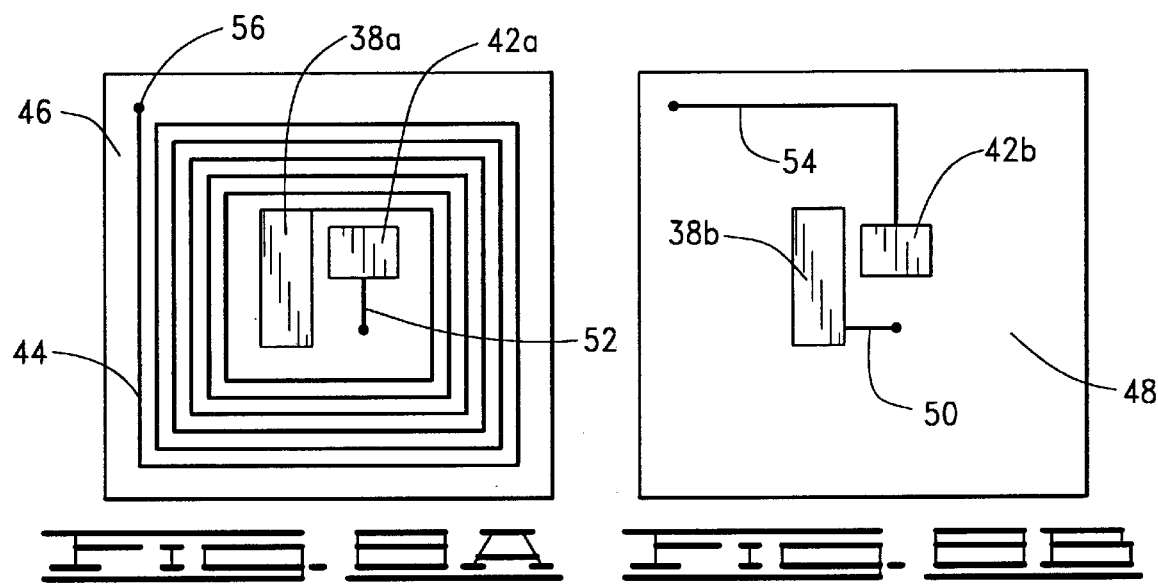
FIGS. 8A–8C illustrate a particular implementation of the medical sensor.
Figure 8C:
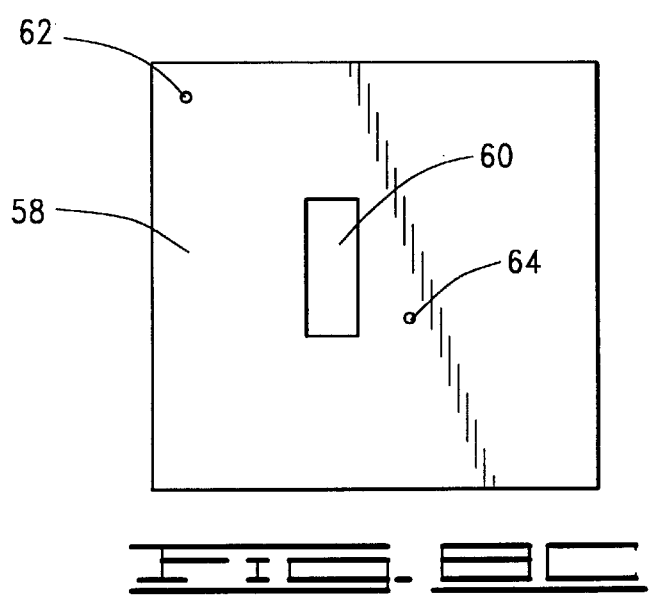

A particular implementation of the circuit of FIG. 7 is illustrated in FIGS. 8A–8C. The part of the circuit shown in FIG. 8A includes a film layer 46 made of a suitable flexible material. One example for the film material is polyester, and a particular implementation of polyester is MELINEX® 505 heat-stabilized polyester film (ICI Films); a crystal clear high gloss film based on MELINEX® 505 can be overprinted with a wide range of solvent-based graphic inks and varnishes, silver conductive and dielectric inks, ideally suited for graphic and certain circuitry layers in membrane touch switches. The film 46 of FIG. 8A is screen-printed with a silver tracing as illustrated to define the winding of the inductor 44. This tracing is continuous in concentric loops inwardly to an electrically conductive member 38a defining one side of the variable capacitance switch 38 of FIG. 7. Also mounted on the film 46 is an electrically conductive member 42a defining one plate of the capacitor 42.

Referring to FIG. 8B, another portion of the implementation of the circuit of FIG. 7 is shown. This includes a film 48 of the same material as the film 46. Screen-printed on the film 48 is an electrically conductive member 38b disposed on a location of the film 48 to mirror the location of the member 38a on the film 46. Likewise, a conductive member 42b mirroring the location of conductive member 42a is applied to the film 48 as shown in FIG. 8B. A silver tracing 50 extends from the member 38b and connects to a silver tracing 52 connected to the member 42a on film 46. A silver tracing 54 extends from the member 42b on the film 48 to a connection with end 56 of the silver tracing defining the inductor 44 on the film 46. The opposite surface of the film 48 has an adhesive on it to adhere to the outer surface of the dressing 10 or directly to the skin of the patient 2. Adhesives suitable for these purposes are known in the art.

When assembled, the film 46 overlies the film 48 with an intervening film 58 (FIG. 8C) disposed between. The film 58 can be made of the same non-conductive material as films 46, 48. The film 58 has a window, or opening, 60 defined through it in between the locations of the facing conductive members 38a, 38b. The aforementioned connections between the silver tracings are made through holes 62, 64 defined in the film 58. The films 46, 48, 50 can be held together by any suitable means, including suitable adhesive applied to the films (e.g., a #200 MP hi-performance acrylic adhesive such as product nos. 7952 MP and 7955 MP from 3M) or by lamination.

With the layer of film 58 between the conductive members 42a, 42b, the intervening portion of the film 58 acts as a dielectric and structural spacer to maintain the capacitor 42 at a fixed value. The conductive members 38a, 38b, on the other hand, are separated only by the air within the window 60 so that in response to pressure the plates can be pressed towards one or the other or together until they touch, thereby defining the minimum capacitance (i.e., short-circuit in this case) state.

The configuration of the components shown in FIG. 8 can vary. For example, instead of the square or rectangular configurations, round or curved configurations can be used. Furthermore, other conductive materials and application techniques can be used in constructing the circuit. For example, foil layers rather than silver traces can be used; however, it is contemplated that other constructions can also be used so long as repeatable pressure responsive actuation of the electrical circuit results. Examples of particular materials and fabrication techniques are known, such as in the field of electronic article surveillance.

It is also contemplated that other types of circuits capable of generating detectable signals without external wire connections can be used. For example, a resonant circuit having an electrically resistant component can be designed using force sensing resistors from Interlink Electronics. One or more of such sensors can be used in a single medical sensor 8. These are mechanically operated with a switch-like response at a specified pressure. A thin stiffener layer, such as Kapton® brand material, can be adhered to each force sensing resistor to minimize false triggering due to bending without adding overall stiffness to the medical sensor. Thus, instead of a capacitor varying as in the FIG. 7 embodiment, the resistance varies to change the circuit characteristic. Another variable characteristic that can be used is inductance. Thus, it is contemplated that any (or multiple) resonant circuit characteristic(s) can be varied.

Although not preferred, a variable circuit element can be used in a battery energized circuit such as a force sensing resistor circuit shown in FIG. 9. When the voltage at the non-inverting input of operational amplifier 66 exceeds the voltage of the inverting input, the output of the operational amplifier toggles to a high logic level. The triggering voltage, and therefore the force threshold, is set at the inverting input by the potentiometer 68. The hysteresis resistor 70 acts as a debouncer, eliminating multiple triggering of the output that might otherwise occur. A force sensing resistor is identified in FIG. 9 by the reference numeral 72.

The operation and method of the present invention will next be described. In accordance with the illustrated embodiments of the present invention, a method of monitoring a pressure sensitive area of a human body comprises changing a characteristic of a resonant circuit, applied to the pressure sensitive area of the human body, in response to movement of the human body causing a pressure due to weight of the human body against a support surface to change (e.g., the patient 2 rolling onto his or her back on the bed 6, or sitting too long immobilized in a chair). This occurs such as with the circuits shown in FIGS. 6 and 7 after the respective medical sensor 8 has been connected to the pressure sensitive area of the human body. As shown in the FIG. 1 illustration, the medical sensor 8 of the preferred embodiment includes the dressing 10 applied to the pressure sensitive area with the electric circuit of the medical sensor attached to the dressing.

In the illustrated embodiments of FIGS. 6 and 7, the changing of the characteristic can be repeated. This occurs by repeatedly operating the switch 38 in the medical sensor 8 between at least two states in response to repeated movement of the human body causing a pressure at the pressure sensitive area due to weight of the human body against a support surface to change repeatedly at least between less than a predetermined pressure magnitude and greater than the predetermined pressure magnitude.

The method further includes energizing, by electromagnetic induction, the resonant circuit of the medical sensor 8 such that the resonant circuit generates a resonant signal dependent on the changed characteristic (e.g., the open or closed state of the switch 38 in FIG. 6 or the changed capacitance value of the switch 38 in FIG. 7). The resonant signal is detected and processed as desired in at least the local controller 30 for the system illustrated in FIG. 4. As mentioned above, the detecting occurs through the receiver 22; however, that function can be implemented in either the unit 20 or the unit 22 shown in FIG. 4 to enable a more comprehensive scanning of the sensing field. For example, if a particular medical sensor 8 is close to the antenna coil of what is marked a transmitter in FIG. 4 and far from the antenna coil of what is marked the receiver in FIG. 4, the resonant signal from the medical sensor 8 may not be strong enough for the farther receiver 22 to detect. By operating the controller 30 to toggle the roles of the units 20, 22 so that the unit 20 becomes the receiver and the unit 22 the transmitter, better reception occurs relative to the medical sensor which is closer to the now receiver functioning unit 20.

From wherever the electromagnetic field 24 is provided, it is established in the vicinity of the human body 2 such that the one or more medical sensors 8 are maintained within the field throughout the movement of the human body on the support. If a single medical sensor 8 is used, the transmitted field 24 can be by way of a radio frequency signal having a single frequency. When multiple medical sensors 8 are used, the electromagnetic field 24 is provided by transmitting radio frequency signals having different respective frequencies within a predetermined frequency range. By way of example, such a predetermined frequency range can be from about six megahertz to about twelve megahertz. These signals can be transmitted concurrently if the receiver is able to respond to concurrently generated resonant signals in response to the multi-frequency electromagnetic field. The radio frequency signals defining the field 24 can be transmitted sequentially such that signals having only one of the different respective frequencies is transmitted at any one time.

With a circuit such as illustrated in FIG. 7, a single frequency driving signal can be transmitted to provide the electromagnetic field 24 and yet receive multiple responsive resonant signals at different frequencies as the switch 38 is affected by pressure. This depends on whether the circuit of FIG. 7 is designed to provide different resonant signals in response to a single or multiple frequency driving signal. For example, the circuit of FIG. 7 can be designed to be resonant at different harmonics which could arise in response to a single frequency driving signal.

In a different configuration, different driving signals can be used to elicit different frequency responses from a circuit of the type illustrated in FIG. 7. For example, a first driving signal is transmitted across a region in which the patient is disposed. This first driving signal has a first frequency to which the sensor 8 of the FIG. 7 type responds in a respective capacitive state of the switch 38. If a response to the first driving signal is received, then a second driving signal is transmitted across the region. The second driving signal has a second frequency to which the sensor 8 responds in at least a second operating state. The foregoing operations can be defined such that detecting this second responsive signal indicates a condition related to the patient, whereas a response to the first driving signal indicates that the sensor is present within the field.

When an operative medical sensor 8 is within the electromagnetic field 24, the sensor propagates resonant signals depending upon the state of the switch 38 for the illustrated embodiments. In a system designed to sense pressure above or below a predetermined magnitude, a signal is transmitted or not in response to pressure below the predetermined magnitude, and a signal is propagated or not in response to pressure above the predetermined magnitude. Such propagated signal is wirelessly communicated to the receiver 22.

A resonant signal is propagated by emitting it from each respective external area of the patient to which a medical sensor is applied. For multiple sensors 8, each one preferably has a respective resonant frequency responsive to a respective frequency of the radio frequency signal defining the energizing electromagnetic field 24.

The transmitter 20 that generates the field 24 is preferably capable of generating radio frequency signals across a selected range of frequencies as mentioned above. At the appropriate driving signal frequency, a respective medical sensor 8 resonates at that frequency to produce the distinctive signal detectable by the receiver relative to the other frequencies transmitted from the transmitter. The receiver 22 is capable of receiving signals across the range of the resonant signals. This enables different sensors 8 to be used and identified by different resonant frequencies, and it also enables an individual sensor 8 to provide different resonant signals in response to different sensed conditions (i.e., different pressure magnitudes in the illustrated embodiments).

By way of a specific example, the circuit of FIGS. 7 and 8 can be used to detect at least three states: no medical sensor 8 present, medical sensor 8 present but pressure below threshold, and medical sensor 8 present with pressure above predetermined threshold. To detect the first condition, no signal is detected because there is no resonant circuit as in FIG. 7 to respond to the energizing electromagnetic field. Sensing the second condition occurs when the conductive members 38a, 38b, shown in FIGS. 8A and 8B, are separated to define a capacitance and thus a first resonant characteristic (due to $C_{38}$, $C_{42}$ and $L_{44}$) for the circuit of FIG. 7. The third condition is detected by the applied pressure closing the conductive members 38a, 38b into contiguous touching, thereby defining a second resonant characteristic (due to $C_{42}$ and $L_{44}$) for the circuit of FIG. 7.

Another embodiment expands the number of detectable medical sensors, their states and meanings by partitioning the frequency range to be applicable to respective medical sensors. This enables multiple medical sensors 8 to be used. In this type of use, each medical sensor 8 responds to a unique frequency band within which respective resonant signals are generated so that they do not overlap with signals or harmonics of other medical sensors used on the same patient. Within each frequency band, pressure-on and pressure-off conditions or different pressure levels can be indicated. More generally, each sensor can simply be said to respond to respective frequencies for which it is designed.

Variable frequency detection can also be useful in accounting for variances arising from manufacturing tolerances in the components of the medical sensors.

When signals are received by the receiver 22 in the FIG. 4 illustration, data is communicated to the controller 30 connected to the resonant signal detector. This can be by any suitable communication technique between the devices. One example is for the controller 30 to poll the receiver 22 for data about each sensor 8 known to be in the field 24. Thus, if a sensor 8 is not present, such as indicated by the three-response embodiment referred to above for FIG. 7, the polling can be expedited by not seeking information for any sensors not used. Polling can also be implemented by the controller 30 periodically activating and deactivating the transmitter and receiver; for example, activating them every minute for a time sufficient (e.g., a few milliseconds or seconds) to transmit across the requisite frequency range and detect any responsive resonant signals.

The communicated information is sufficient for the controller 30 to determine the amount of time that pressure above the predetermined magnitude existed and the number of changes between pressure above the predetermined magnitude and pressure below the predetermined magnitude. In one type of communication, the information is simply the detected resonant signal or the absence of such signal as the case may be; that is, if the receiver 22 is essentially a filter (or multiple filters) tuned to detect a respective resonant signal, the information communicated to the controller 30 is the output of the filter.

An exposure time value relative to the respective pressure sensitive area can be computed with the controller 30. The exposure time value is computed in response to a predetermined monitoring period and the cumulative time within the monitoring period during which pressure greater than the predetermined magnitude existed at the respective area. This is determined from the pressure-on signals received in the controller from the receiver 22. Whenever the controller 30 receives a resonant signal output from the receiver 22, the controller 30, accordingly constructed or programmed, interprets it as a pressure-on; if no signal is received, the controller 30 interprets a pressure-off. The cumulative information during a respective monitoring period is used to compute the exposure time.

Information in the controller 30 can also be used to compute a shift frequency value in response to the respective predetermined shift frequency monitoring period and the number of changes between pressure above the predetermined magnitude and pressure below the predetermined magnitude. The number of changes can be determined from the aforementioned signals in that the controller 30 computes how many transitions between pressure-on and pressure-off and between pressure-off and pressure-on during the period.

As described above, the aforementioned communication includes signals being sent from the receiver 22 to the controller 30 to indicate on and off conditions for the simplified pressure-on/pressure-off condition sensing of the circuit of FIG. 6 or for the circuit of FIG. 7 operating in the aforementioned three states (not present/operative, first operative state, second operative state). For the FIG. 6 embodiment, for example, when a pressure above the predetermined threshold is indicated by the receiver receiving a respective resonant signal of the appropriate frequency, this signal is passed on to the controller 30. From these signals, which indicate pressure-on or pressure-off at the particular time of sensing, the controller determines cumulative pressure-on and pressure-off events (if done by sampling over time, it is assumed transitions did not occur within the interim between samples; therefore, sampling, or polling, rates should be sufficiently fast (i.e., sufficiently short time between samples). The result of the cumulative determination by the controller 30 can be represented by pulses such as illustrative pulses 74, 76, 78 shown in FIG. 10. The duration of each of these pulses corresponds to the length of time of a "pressure-on" event in which pressure above the threshold is continuously applied to the respective switch 38 and thus to the respective pressure sensitive area. The intervening times between the pulses correspond to "pressure-off" events. Each transition from an on state to an off state or from an off state to an on state signifies a shift by the patient 2 causing the change in the amount of pressure applied to the respective medical sensor 8.

The information provided to the local controller 30 is transferred by suitable communication, such as RS232 serial communication. The controller 30 accumulates the time spent in both pressure-on and pressure-off events. The number of shifts as indicated by the aforementioned signal transitions are also recorded. The controller 30 also logs time to define one or more monitoring periods in seconds or minutes, for example. This information is logged with unique identification information to correlate the data to a respective medical sensor and patient. The information from the controller 30 can be transferred to the computer 18 for use by the overall network illustrated in FIG. 5, for example. Compatibility with a Windows 95 or similar environment in the computer 18 is preferred to allow for organization of subject data in a spreadsheet format. Communication from the controller 30 to the computer 18 is by a suitable technique, preferably a conventional technique such as serial RS232 communication. In general, the system of FIG. 5 preferably uses conventional networking communications. Data can be reported such as illustrated in FIG. 11 (the last information, "average pressure," being available if different applied pressure levels are sensed).

From this information, exposure time and shift frequency values can be determined as mentioned above. Exposure time (ET) is defined as the percent of time spent in a pressure-on condition (ON, in desired time units, for example, seconds) during the monitoring period (MP, in corresponding time units):

$$ET\ (\%) = (ON/MP) \times (100).$$

Shift frequency (SF) is the number of shifts (NOS, defined by on-off and off-on transitions for the FIG. 10 illustration) per monitoring period (MP, in desired time units, for example, hours):

$$SF=NOS/MP$$

The exposure time and shift frequency values are used to define relationships with regard to the formation of ulcers and the healing of ulcers. With such information, the patient can be treated, such as by moving the patient in response to the computed shift frequency value and the exposure time value. These can be used in a computer-implemented pressure ulcer management method of the present invention as next described.

For the illustrated embodiments, the pressure ulcer management method comprises maintaining in the controller 30 or computer 18 (FIGS. 4 and 5) a database containing a respective predetermined ulceration event for one or more patients. This database particularly contains a respective ulceration history for each patient. Each ulceration history includes data identifying one or more of the following indicative of or relevant to a patient's susceptibility to ulcer formation.

overall risk assessment evaluations (e.g., Norton, Braden, Gosnell, or Knoll scales)

individual factor analysis (e.g., age, malnourishment, immobilization, infection, poor hygiene, neurologic deficits (spinal cord injury, state of consciousness, sedation, etc.), skin condition, incontinence, heart disease, diabetes, peripheral vascular disease)

unhealed ulcers previous ulcers the number of previous ulcers occurring at the same location of the respective patient when each previous ulcer was detected at the respective location when each previous ulcer was healed the number of pressure applications (preferably including SF) sensed during the period between when a respective previous ulcer was detected and when the respective previous ulcer was healed the cumulative exposure time (preferably including ET) to pressure during the period between when a respective previous ulcer was detected and when the respective previous ulcer was healed the number of pressure applications (preferably including SF) sensed during the period between when a respective previous ulcer was healed and when the next ulcer at the same respective location was detected the cumulative exposure time (preferably including ET) to pressure during the period between when a respective previous ulcer was healed and when the next ulcer at the same respective location was detected.

The ulcer management method also comprises monitoring the patient(s). This includes for each patient, sensing pressure application to at least one location on the respective patient at risk to ulcer formation, and communicating data to the computer defining shifts of the respective patient between pressure-on and pressure-off events relative to the at least one location. If an unhealed ulcer exists at the location, this includes sensing pressure application to each unhealed ulcer. If the location is presently healed but the site of one or more previous ulcers, this includes sensing pressure application to the previous ulcer location and communicating data to the computer in response to the sensed pressure applications. The data is stored in the computer with data already in the database.

The data stored in the computer includes the number of pressure applications and a cumulative exposure time to pressure for each unhealed ulcer. The data further includes the number of pressure applications to a respective location of previous ulceration and a cumulative exposure time to pressure for each such location since the last previous ulcer was healed at that location.

The method can further comprise managing the care of each patient in response to that patient's respective ulceration history and the respective stored additional data. This can include computing an estimated remaining treatment period for a respective unhealed ulcer in response to the historical data for at least one previous ulcer of the patient and the additional current data for the respective unhealed ulcer. For example, an average healing rate or other value determined from the historical data can be computed (e.g., as an averaged time between when respective ulcers were detected and when they were healed; or, as another example, as an averaged historical cumulative exposure time and/or number of shifts, with or without averaged time as in the preceding example) and compared with a corresponding value determined since detecting the then-existing ulcer.

With respect to prevention of ulcers, managing the care of each patient can further comprise determining in the computer a respective frequency of ulcer formation in response to the historical data for each location (e.g., any of the aforementioned averages of absolute time, cumulative exposure time, or number of shifts computed relative to the number of ulcers that have formed at a particular location). This further comprises determining in the computer a respective time since the last previous ulcer was healed at each respective location for the respective patient and comparing the determined time with the respective determined frequency of ulcer formation for the respective location.

The foregoing can be combined in managing the care of a respective patient. For example, treatment can include comparing (1) the number of pressure applications to a respective one of the locations of previous ulcers and the cumulative exposure time to pressure for each such location since the last previous ulcer was healed at each respective location for the patient with (2) pressure applications sensed during the period between when a respective previous ulcer was healed and when the next ulcer at the same respective location was detected and the cumulative exposure time to pressure during the period between when the respective previous ulcer was healed and when the next ulcer at the same respective location was detected.

From the foregoing, a predetermined ulceration event can include a time or other event at which the respective patient is to be turned relative to a respective location susceptible to ulceration. The predetermined ulceration event can also or alternatively include a pressure-on threshold (e.g., pressure above a threshold has occurred, or pressure above the threshold for a continuous time period or a cumulative time, or number of shifts between pressure-on and pressure-off) relative to a respective location susceptible to ulceration. The ulcer management method can then further comprise correlating in the computer the communicated data, representing current and at least recent conditions at the location, with the respective predetermined ulceration event for each of the patients. For the foregoing events, this includes determining whether a transition from a pressure-on event to a pressure-off event occurred at the respective time to determine whether the event occurred at the time the respective patient was to be turned, thereby indicating whether compliance with the turning schedule has been made. This can also or alternatively include determining the length of time since detecting a sensed pressure exceeding the predetermined pressure-on threshold until the next sensed pressure-off event as an indication of compliance or not with the patient staying in a pressure-on condition exceeding the pressure-on threshold for a continuous time.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A medical sensor responsive to a predetermined condition, the sensor providing wireless communication of the sensing of the condition, comprising:
   a substrate applicable to the outside of a human body; and
   an electric circuit connected to the substrate, including:
      a switch operable in a circuit operative state in response to the predetermined condition, wherein the predetermined condition is pressure against the outside of the human body at a location thereof to which the substrate is applied; and
      resonant circuit elements connected to the switch as a resonant circuit to provide a signal at a resonant frequency in response to electromagnetic induction, originating from outside the electric circuit, when the switch is in the circuit operative state.

2. A medical sensor as defined in claim 1, wherein the substrate includes an adhesive portion adapted to adhere to the human body at a location susceptible to decubitus ulceration.

3. A medical sensor as defined in claim 1, wherein the switch is in a different operative state when not responding to the predetermined condition such that the resonant circuit provides a signal at another resonant frequency in response to electromagnetic induction when the switch is in the different operative state.

4. A medical sensor as defined in claim 1, wherein the switch has a variable capacitance responsive to the magnitude of the predetermined condition.

5. A medical sensor providing wireless communication of the sensing of a human body pressure condition, comprising:
   a dressing applicable to a human body at a decubitus ulcer site or a site susceptible to developing a decubitus ulcer; and
   a pressure responsive circuit connected to the dressing, including:
      a switch repeatably operable between a first state and a second state in response to whether pressure above a predetermined threshold is applied by at least partial weight of the human body when the dressing is applied to the human body; and
      resonant circuit elements connected to the switch to define on the dressing a self-contained resonant circuit.

6. A medical sensor as defined in claim 5, wherein the pressure responsive circuit further includes an adhesive member adhered to the dressing, the adhesive member having the switch and the resonant circuit elements mounted thereon.

7. A medical sensor as defined in claim 6, wherein the switch includes two electrically conductive members spaced in the first state to define a capacitance and contiguous in the second state to define a short-circuit.

8. A medical sensor as defined in claim 5, wherein the switch includes two electrically conductive members spaced in the first state to define a capacitance and contiguous in the second state to define a short-circuit.

9. A medical sensor responsive to an external human body pressure condition, comprising:
   a switch operable in a circuit operative state in response to pressure applied to the outside of a human body;
   resonant circuit elements connected to the switch to define a resonant circuit responsive to an electromagnetic field originating outside the sensor at least when the switch is in the circuit operative state; and
   means for attaching the switch and the resonant circuit elements to the outside of the human body such that the switch is exposed to an occurrence of the pressure applied to the outside of the human body.

10. A medical sensor as defined in claim 9, wherein the means for attaching includes an adhesive member having the switch and the resonant circuit elements mounted thereon.

11. A medical sensor responsive to a predetermined condition, comprising:
    a switch operable in a circuit operative state in response to the predetermined condition;
    resonant circuit elements connected to the switch to define a resonant circuit responsive to electromagnetic induction at least when the switch is in the circuit operative state; and
    means for attaching the switch and the resonant circuit elements relative to a human body such that the switch is exposed to an occurrence of the predetermined condition;
    wherein the predetermined condition is a predetermined pressure magnitude created by at least partial weight of the human body applied at a predetermined location of the human body against a support surface and further wherein the means for attaching is adapted to attach at the predetermined location of the human body such that at least the switch is between the human body and the support surface when the predetermined pressure magnitude is exceeded at the predetermined location.

12. A medical sensor as defined in claim 11, wherein the switch includes a variable capacitor operable between a maximum capacitance state and a minimum capacitance state in response to a change between pressure less than the predetermined pressure magnitude and pressure greater than the predetermined pressure magnitude as the human body shifts relative to the support surface.

13. A method of monitoring pressure applied to a pressure sensitive area of a human body, comprising:
    connecting a medical sensor to the pressure sensitive area of the human body;
    repeatedly operating a switch in the medical sensor between at least two states in response to repeated movement of the human body causing a pressure at the pressure sensitive area due to at least partial weight of the human body against a support surface to change repeatedly at least between less than a predetermined pressure magnitude and greater than the predetermined pressure magnitude, wherein the switch is connected in a resonant circuit in the medical sensor; and
    detecting a respective resonant electromagnetic wave signal generated in response to operating the switch in each of the states.

14. A method as defined in claim 13, wherein connecting the medical sensor to the pressure sensitive area includes attaching an electric circuit of the medical sensor to a dressing of the medical sensor applied to the pressure sensitive area.

15. A method as defined in claim 14, further comprising providing in the vicinity of the human body an electromagnetic field within which the medical sensor connected to the human body is disposed throughout the movement of the human body.

16. A method as defined in claim 15, wherein repeatedly operating a switch includes repeatedly changing the capacitance of a capacitor in the medical sensor.

17. A method as defined in claim 13, wherein repeatedly operating a switch includes repeatedly changing the switch between a capacitive state and a short-circuit state.

18. A system to monitor a pressure sensitive area of a patient positioned on a support, comprising:
    an electromagnetic wave transmitter disposed adjacent the support;
    a resonant signal detector disposed adjacent the support in operative association with the electromagnetic wave transmitter;
    a medical sensor adapted to be attached to the patient such that the medical sensor is responsive to pressure applied to the pressure sensitive area of the patient, the medical sensor including a resonant circuit operative in at least two states in response to pressure applied to the pressure sensitive area of the patient, in at least one of the states the resonant circuit causing a resonant signal to be propagated in cooperative operation with the electromagnetic wave transmitter, wherein the medical sensor is not tangibly attached to the electromagnetic wave transmitter or the resonant signal detector when the medical sensor is attached to the patient; and
    a controller connected to the resonant signal detector such that the controller receives a respective signal from the resonant signal detector in response to the resonant signal detector detecting a respective propagated resonant signal, wherein the controller computes an exposure time value in response to a predetermined exposure time monitoring period and a cumulative time within the exposure time monitoring period during which the controller receives signals from the resonant signal detector indicating pressure applied to the pressure sensitive area greater than a predetermined magnitude.

19. A system as defined in claim 18, wherein the controller computes a shift frequency value in response to a predetermined shift frequency monitoring period and the number of transitions relative to receiving signals from the resonant signal detector during the shift frequency monitoring period.

20. A system to monitor a pressure sensitive area of a patient positioned on a support, comprising:
    an electromagnetic wave transmitter disposed adjacent the support;
    a resonant signal detector disposed adjacent the support in operative association with the electromagnetic wave transmitter;
    a medical sensor adapted to be attached to the patient such that the medical sensor is responsive to pressure applied to the pressure sensitive area of the patient, the medical sensor including a resonant circuit operative in at least two states in response to pressure applied to the pressure sensitive area of the patient, in at least one of the states the resonant circuit causing a resonant signal to be propagated in cooperative operation with the electromagnetic wave transmitter, wherein the medical sensor is not tangibly attached to the electromagnetic wave transmitter or the resonant signal detector when the medical sensor is attached to the patient; and
    a controller connected to the resonant signal detector such that the controller receives a respective signal from the resonant signal detector in response to the resonant signal detector detecting a respective propagated resonant signal, wherein the controller is programmed to compute a shift frequency value in response to a predetermined monitoring period and the number of transitions relative to receiving signals from the resonant signal detector during the monitoring period.

21. A system to monitor a plurality of external pressure sensitive areas of a patient lying on a bed, comprising:
    a variable frequency electromagnetic wave transmitter disposed to one side of the bed;
    a resonant signal detector disposed to another side of the bed in operative association with the electromagnetic wave transmitter such that an electromagnetic field generated by the transmitter exists between the transmitter and the detector;
    a plurality of medical sensors, wherein each of the medical sensors is adapted to attach to the patient at a respective external pressure sensitive area susceptible to decubitus ulceration, each of the medical sensors includes a respective resonant circuit operative in at least two states in response to pressure applied to the respective medical sensor, in at least one of the states the respective resonant circuit causing a respective resonant signal to be propagated in cooperative operation with the electromagnetic wave transmitter and the electromagnetic field generated by the transmitter; and
    a controller connected to the resonant signal detector such that the controller receives a respective signal from the resonant signal detector in response to the resonant signal detector detecting each propagated resonant signal.

22. A system to monitor a plurality of pressure sensitive areas of a patient lying on a bed, comprising:
    a variable frequency electromagnetic wave transmitter disposed to one side of the bed;
    a resonant signal detector disposed to another side of the bed in operative association with the electromagnetic wave transmitter such that an electromagnetic field generated by the transmitter exists between the transmitter and the detector;
    a plurality of medical sensors, wherein each of the medical sensors is adapted to attach to the patient at a respective pressure sensitive area susceptible to decubitus ulceration, each of the medical sensors includes a respective resonant circuit operative in at least two states in response to pressure applied to the respective medical sensor, in at least one of the states the respective resonant circuit causing a respective resonant signal to be propagated in cooperative operation with the electromagnetic wave transmitter and the electromagnetic field generated by the transmitter; and
    a controller connected to the resonant signal detector such that the controller receives a respective signal from the resonant signal detector in response to the resonant signal detector detecting each propagated resonant signal;
    wherein the controller is programmed to compute an exposure time value relative to each of the medical sensors, wherein the exposure time value for each medical sensor is computed in response to a predetermined exposure time monitoring period and a cumulative time within the exposure time monitoring period during which the controller receives signals from the resonant signal detector indicating pressure applied to the respective medical sensor greater than a predetermined magnitude.

23. A system as defined in claim 22, wherein the controller is further programmed to compute, relative to each of the medical sensors, a shift frequency value in response to a predetermined shift frequency monitoring period and the number of transitions in signals received from the resonant signal detector during the shift frequency monitoring period for the respective medical sensor.

24. A system to monitor a plurality of pressure sensitive areas of a patient lying on a bed, comprising:
- a variable frequency electromagnetic wave transmitter disposed to one side of the bed;
- a resonant signal detector disposed to another side of the bed in operative association with the electromagnetic wave transmitter such that an electromagnetic field generated by the transmitter exists between the transmitter and the detector;
- a plurality of medical sensors, wherein each of the medical sensors is adapted to attach to the patient at a respective pressure sensitive area susceptible to decubitus ulceration, each of the medical sensors includes a respective resonant circuit operative in at least two states in response to pressure applied to the respective medical sensor, in at least one of the states the respective resonant circuit causing a respective resonant signal to be propagated in cooperative operation with the electromagnetic wave transmitter and the electromagnetic field generated by the transmitter; and
- a controller connected to the resonant signal detector such that the controller receives a respective signal from the resonant signal detector in response to the resonant signal detector detecting each propagated resonant signal;
- wherein the controller is programmed to compute, relative to each of the medical sensors, a shift frequency value in response to a predetermined monitoring period and the number of transitions in signals received from the resonant signal detector during the monitoring period for the respective sensor.

25. A method of monitoring one or more pressure sensitive areas of a patient on a support, comprising:
- providing an electromagnetic field across a region of the patient on the support; and
- propagating, in operative association with the electromagnetic field, resonant signals in response to pressure above a predetermined magnitude at one or more external areas of the patient susceptible to ulceration and wirelessly communicating the resonant signals to a resonant signal detector disposed adjacent the support.

26. A method as defined in claim 25, further comprising communicating signals to a controller connected to the resonant signal detector, and determining with the controller the amount of time that pressure above the predetermined magnitude existed and the number of changes between pressure above the predetermined magnitude and pressure below the predetermined magnitude.

27. A method as defined in claim 26, further comprising computing with the controller an exposure time value relative to the one or more external areas of the patient susceptible to ulceration, wherein the exposure time value for each medical sensor is computed in response to a predetermined exposure time monitoring period and the cumulative time within the exposure time monitoring period during which pressure greater than the predetermined magnitude existed at the respective area.

28. A method as defined in claim 27, further comprising computing, with the controller and relative to the one or more external areas of the patient susceptible to ulceration, a shift frequency value in response to a predetermined shift frequency monitoring period and the number of changes between pressure above the predetermined magnitude and pressure below the predetermined magnitude.

29. A method as defined in claim 26, further comprising computing, with the controller and relative to the one or more external areas of the patient susceptible to ulceration, a shift frequency value in response to a predetermined monitoring period and the number of changes between pressure above the predetermined magnitude and pressure below the predetermined magnitude.

30. A method as defined in claim 25, wherein:
- providing an electromagnetic field includes transmitting radio frequency signals having different respective frequencies within a predetermined frequency range; and
- propagating resonant signals includes emitting from each respective external area resonant signals having a respective resonant frequency responsive to a respective frequency of the radio frequency signals.

31. A method as defined in claim 30, wherein the radio frequency signals are transmitted concurrently.

32. A method as defined in claim 30, wherein the radio frequency signals are transmitted sequentially such that signals having only one of the different respective frequencies is transmitted at a time.

33. A method as defined in claim 30, further comprising propagating, in operative association with the electromagnetic field, different resonant signals in response to pressure below the predetermined magnitude at any of the one or more external areas of the patient susceptible to ulceration and wirelessly communicating the different resonant signals to the resonant signal detector.

34. A method as defined in claim 33, wherein propagating resonant signals and propagating different resonant signals include operating a switch in a resonant circuit at a respective one of the external areas between a short-circuit condition and a capacitance condition of the switch in response to pressure applied to the switch.

35. A method as defined in claim 25, further comprising propagating, in operative association with the electromagnetic field, different resonant signals in response to pressure below the predetermined magnitude at any of the one or more external areas of the patient susceptible to ulceration and wirelessly communicating the different resonant signals to the resonant signal detector.

36. A method as defined in claim 35, wherein propagating resonant signals and propagating different resonant signals include operating a switch in a resonant circuit at a respective one of the external areas between a short-circuit condition and a capacitance condition of the switch in response to pressure applied to the switch.

37. A method as defined in claim 25, wherein providing an electromagnetic field includes generating, at a first time, the electromagnetic field from a first location relative to the region and generating, at a second time, the electromagnetic field from a second location relative to the region.

38. A method as defined in claim 31, wherein providing an electromagnetic field includes periodically actuating a transmitter to generate the electromagnetic field temporarily so that the electromagnetic field is not constantly present across the region of the patient or the support.

39. A method of monitoring for a pressure sensor adapted to be attached externally to a patient, comprising:
- transmitting, across a region in which a patient is disposed, a driving signal having at least one frequency to which a pressure sensor adapted to be attached externally to the patient is responsive if the pressure sensor is attached to the patient and operational;
- detecting whether a first response signal is emitted from the sensor in the region in response to the driving signal, the first response signal indicating the presence of the operational sensor in the region;
- detecting whether a second response signal is emitted from the sensor in the region in response to the driving signal, the second response signal indicating an external pressure condition related to the patient; and
- repeating the transmitting and detecting steps for respective selected frequencies of the driving signal and respective responsive frequencies for the first and second response signals for a plurality of sensors adapted to be attached to the patient such that each sensor is uniquely identified.

40. A method of monitoring for a pressure sensor adapted to be attached externally to a patient, comprising:

transmitting, across a region in which a patient is disposed, a driving signal having at least one frequency to which a pressure sensor adapted to be attached externally to the patient is responsive if the pressure sensor is attached to the patient and operational;

detecting whether a first response signal is emitted from the sensor in the region in response to the driving signal, the first response signal indicating the presence of the operational sensor in the region; and detecting whether a second response signal is emitted from the sensor in the region in response to the driving signal, the second response signal indicating an external pressure condition related to the patient;

wherein the driving signal is transmitted from different locations relative to the region and wherein detecting occurs from different locations relative to the region such that the first and second response signals are within detection range of at least one of the locations.

41. A method of monitoring for a pressure sensor adapted to be attached externally to a patient, comprising:

transmitting, across a region in which a patient is disposed, a driving signal having at least one frequency to which a pressure sensor adapted to be attached externally to the patient is responsive if the pressure sensor is attached to the patient and operational;

detecting whether a first response signal is emitted from the sensor in the region in response to the driving signal, the first response signal indicating the presence of the operational sensor in the region; and detecting whether a second response signal is emitted from the sensor in the region in response to the driving signal, the second response signal indicating an external pressure condition related to the patient;

wherein transmitting the driving signal includes sequentially providing the driving signal from different locations relative to the region and wherein detecting occurs from different locations relative to the region such that the first and second response signals are within detection range of at least one of the locations.

42. A method of monitoring for a sensor adapted to be attached to a patient, comprising:

transmitting, across a region in which a patient is disposed, a first driving signal having a first frequency to which a sensor adapted to be attached to the patient is responsive if the sensor is attached to the patient and if the sensor is in at least a first operating state;

detecting whether a first response signal is emitted from the sensor in the region in response to the first driving signal;

in response to detecting the first response signal, transmitting across the region a second driving signal having a second frequency to which the sensor is responsive in at least a second operating state; and detecting whether a second response signal is emitted from the sensor in response to the second driving signal, the second response signal indicating a condition related to the patient.

43. A method of monitoring a pressure sensitive area of a patient on a support, comprising:

communicating signals indicating (1) that pressure above a predetermined magnitude has been exerted against the pressure sensitive area and (2) changes between pressure above the predetermined magnitude and pressure below the predetermined magnitude;

computing a shift frequency value in response to a predetermined shift frequency monitoring period and the number of changes between pressure above the predetermined magnitude and pressure below the predetermined magnitude occurring during the predetermined shift frequency monitoring period as indicated by the communicated signals; and moving the patient in response to the computed shift frequency value.

44. A method as defined in claim 43, further comprising computing an exposure time value, wherein the exposure time value is computed in response to a predetermined exposure time monitoring period and the cumulative time within the exposure time monitoring period during which pressure greater than the predetermined magnitude was exerted against the pressure sensitive area as indicated by the communicated signals, and moving the patient in response to both the computed shift frequency value and the computed exposure time value.

45. A computer-implemented pressure ulcer management method, comprising:

maintaining in a computer a database containing a respective ulceration history for each of a plurality of patients, each ulceration history including data identifying information relevant to the respective patient's susceptibility to ulcer formation;

monitoring the patients, including for each patient sensing pressure application to at least one location on the respective patient at risk to ulcer formation and communicating additional data to the computer in response to sensed pressure application;

storing in the computer the additional data with the data in the database; and managing the care of each patient in response to that patient's respective ulceration history and the respective stored additional data.

46. A method as defined in claim 45, wherein the additional data includes for each patient the number of pressure applications and a cumulative exposure time to pressure for the at least one location on the respective patient at risk to ulcer formation.

47. A method as defined in claim 45, wherein each ulceration history further includes respective patient historical data identifying any unhealed ulcers, previous ulcers, when each previous ulcer was detected, when each previous ulcer was healed, the number of pressure applications sensed during the period between when a respective previous ulcer was detected and when the respective previous ulcer was healed, and the cumulative exposure time to pressure during the period between when a respective previous ulcer was detected and when the respective previous ulcer was healed.

48. A method as defined in claim 47, wherein:

the additional data includes the number of pressure applications and a cumulative exposure time to pressure for each unhealed ulcer; and managing the care of each patient includes computing an estimated remaining treatment period for a respective unhealed ulcer in response to the historical data for at least one previous ulcer of the patient and the additional data for the respective unhealed ulcer.

49. A method as defined in claim 45, wherein each ulceration history further includes historical data identifying previous ulcers, the number of previous ulcers occurring at the same location of the respective patient, when each previous ulcer was detected at the respective location, and when each previous ulcer was healed.

50. A method as defined in claim 49, wherein:

managing the care of each patient includes determining in the computer a respective frequency of ulcer formation in response to the historical data for each location; and managing the care of each patient further includes determining in the computer a respective time since the last previous ulcer was healed at each respective location for the respective patient and comparing the determined time with the respective determined frequency of ulcer formation for the respective location.

51. A method as defined in claim 49, wherein:

the historical data further identifies pressure applications sensed during the period between when a respective previous ulcer was healed and when the next ulcer at the same respective location was detected and the cumulative exposure time to pressure during the period between when the respective previous ulcer was healed and when the next ulcer at the same respective location was detected;

the additional data includes the number of pressure applications to a respective one of the locations of previous ulcers and a cumulative exposure time to pressure for each such location since the last previous ulcer was healed at each respective location for the patient; and managing the care of each patient further includes comparing (1) the number of pressure applications to a respective one of the locations of previous ulcers and the cumulative exposure time to pressure for each such location since the last previous ulcer was healed at each respective location for the patient with (2) pressure applications sensed during the period between when a respective previous ulcer was healed and when the next ulcer at the same respective location was detected and the cumulative exposure time to pressure during the period between when the respective previous ulcer was healed and when the next ulcer at the same respective location was detected.

52. A computer-implemented pressure ulcer management method, comprising:

maintaining in a computer a database containing a respective ulceration history for each of a plurality of patients, each ulceration history including historical data identifying previous ulcers, the number of previous ulcers occurring at the same location of the respective patient, when each previous ulcer was detected at the respective location, and when each previous ulcer was healed;

monitoring the patients, including for each patient sensing pressure application to each previous ulcer location identified by the data in the database and communicating additional data to the computer in response to sensed pressure application; and storing in the computer the additional data with the data in the database.

53. A method as defined in claim 52, further comprising:

determining in the computer a respective frequency of ulcer formation in response to the historical data for each location; and determining in the computer, for each patient, a respective time since the last previous ulcer was healed at each respective location for the respective patient and comparing the determined time with the respective determined frequency of ulcer formation for the respective location.

54. A method as defined in claim 52, wherein:

the historical data further identifies pressure applications sensed during the period between when a respective previous ulcer was healed and when the next ulcer at the same respective location was detected and the cumulative exposure time to pressure during the period between when the respective previous ulcer was healed and when the next ulcer at the same respective location was detected;

the additional data includes the number of pressure applications to a respective one of the locations of previous ulcers and a cumulative exposure time to pressure for each such location since the last previous ulcer was healed at each respective location for the patient; and the method further comprises, for each patient, comparing (1) the number of pressure applications to a respective one of the locations of previous ulcers and the cumulative exposure time to pressure for each such location since the last previous ulcer was healed at each respective location for the patient with (2) pressure applications sensed during the period between when a respective previous ulcer was healed and when the next ulcer at the same respective location was detected and the cumulative exposure time to pressure during the period between when the respective previous ulcer was healed and when the next ulcer at the same respective location was detected.

55. A computer-implemented pressure ulcer management method, comprising:

maintaining in a computer a database containing a respective predetermined ulceration event for each of a plurality of patients;

monitoring the patients, including for each patient sensing pressure application to at least one location of the respective patient susceptible to ulceration and communicating data to the computer defining shifts of the respective patient between pressure-on and pressure-off events relative to the at least one location in response to sensed pressure application; and correlating in the computer the communicated data with the respective predetermined ulceration event for each of the patients.

56. A method as defined in claim 55, wherein:

the predetermined ulceration event includes a time the respective patient is to be turned relative to the respective at least one location susceptible to ulceration; and correlating the communicated data with the respective predetermined ulceration event includes determining whether a transition from a pressure-on event to a pressure-off event occurred at the respective time.

57. A method as defined in claim 55, wherein:

the predetermined ulceration event includes a pressure-on threshold relative to the respective at least one location susceptible to ulceration; and correlating the communicated data with the respective predetermined ulceration event includes determining the length of time from a sensed pressure exceeding the predetermined pressure-on threshold to the next sensed pressure-off event.

\* \* \* \* \*

UNITED STATES PATENT AND TRADEMARK OFFICE
CERTIFICATE OF CORRECTION

PATENT NO.     : 6,287,253 B1
DATED          : September 11, 2001
INVENTOR(S)    : Giovani M. Ortega, George B. Schwabe, IV and John A. Sabolich It is certified that error appears in the above-identified patent and that said Letters Patent is hereby corrected as shown below:

<u>Title page,</u>
Item [73], Assignee, after "Development," insert -- Inc. --.
Item [56], References Cited, under U.S. PATENT DOCUMENTS, first reference, delete "Guskaov" and insert -- Gusakov -- therefor.
Under OTHER PUBLICATIONS, fourth reference, delete "Pressure$^{TM}$" and insert -- Pressore$^{TM}$ -- therefor.

<u>Column 7,</u>
Line 19, delete "Restorer" and insert -- Restore$^{TM}$ -- therefor.

<u>Column 24,</u>
Line 46, delete "31" and insert -- 25 -- therefor.

Signed and Sealed this

Sixth Day of August, 2002

*Attest:*

JAMES E. ROGAN
*Attesting Officer*           *Director of the United States Patent and Trademark Office*